(12) United States Patent
Holmquist et al.

(10) Patent No.: US 8,173,442 B2
(45) Date of Patent: *May 8, 2012

(54) METHODS FOR DETECTING DIHYDROXYVITAMIN D METABOLITES BY MASS SPECTROMETRY

(75) Inventors: Brett Holmquist, West Hills, CA (US); Nigel J. Clarke, Oceanside, CA (US); Anne Caston-Balderrama, San Pedro, CA (US); Richard E. Reitz, San Clemente, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/117,997

(22) Filed: May 27, 2011

(65) Prior Publication Data

US 2011/0226945 A1 Sep. 22, 2011

(51) Int. Cl.
*G01N 24/00* (2006.01)
(52) U.S. Cl. ...................................................... 436/173
(58) Field of Classification Search .................. 436/173
See application file for complete search history.

(56) References Cited

U.S. PATENT DOCUMENTS

| | | | |
|---|---|---|---|
| 5,772,874 | A | 6/1998 | Quinn et al. |
| 5,795,469 | A | 8/1998 | Quinn et al. |
| 5,919,368 | A | 7/1999 | Quinn et al. |
| 5,968,367 | A | 10/1999 | Quinn et al. |
| 6,107,623 | A | 8/2000 | Bateman et al. |
| 6,124,137 | A | 9/2000 | Hutchens et al. |
| 6,204,500 | B1 | 3/2001 | Whitehouse et al. |
| 6,268,144 | B1 | 7/2001 | Koster |
| 6,787,660 | B1 * | 9/2004 | Armbruster et al. .......... 552/653 |
| 6,977,143 | B1 | 12/2005 | Caulfield et al. |
| 7,087,395 | B1 | 8/2006 | Garrity et al. |
| 7,321,116 | B2 | 1/2008 | Picard et al. |
| 7,348,137 | B2 | 3/2008 | Caulfield et al. |
| 7,473,560 | B2 | 1/2009 | Soldin |
| 7,618,827 | B2 | 11/2009 | Steven |
| 7,745,226 | B2 | 6/2010 | Clarke et al. |
| 2003/0171605 | A1 | 9/2003 | Reddy et al. |
| 2004/0235193 | A1 | 11/2004 | Soldin |
| 2006/0054807 | A1 | 3/2006 | Picard et al. |
| 2006/0094125 | A1 | 5/2006 | Singh et al. |
| 2006/0228808 | A1 | 10/2006 | Clarke et al. |
| 2006/0228809 | A1 | 10/2006 | Clarke et al. |
| 2007/0139956 | A1 | 6/2007 | Sugimoto et al. |
| 2008/0241955 | A1 | 10/2008 | Purkayastha et al. |
| 2009/0137056 | A1 | 5/2009 | Holmquist et al. |

FOREIGN PATENT DOCUMENTS

| | | |
|---|---|---|
| WO | WO-95/33279 | 12/1995 |
| WO | WO-96/18618 | 6/1996 |
| WO | WO-2007/039193 | 4/2007 |
| WO | WO-2007/139956 | 12/2007 |
| WO | WO-2008/097246 | 8/2008 |

OTHER PUBLICATIONS

Higashi et al. "Simultaneous Determination of 25-Hydroxyvitamin D2 and 25-Hydroxyvitamin D3 in Human Plasma by Liquid Chromatography-Tandem Mass Spectrometry Employing Derivatization with a Cookson-Type Reagent".*
Armas et. al, Vitamin D2 Is Much Less Effective than Vitamin D3 in Humans, J. Clin. Endocrinol. Metab. 89:5387-5391 (2004).
Aronov et al, Metabolic profiling of major vitamin D metabolites using Diels-Alder derivatization and ultra-performance liquid chromatography-tandem mass spectrometry, Anal Bioanal Chem, 2008, 391:1917-1930.
Ascalone et al, Stereospecific determination of amisulpride, a new benzamide derivative, in human plasma and urine by automated solid-phase extraction and liquid chromatography on a chiral column. application to pharmacokinetics, Journal of Chromatography B., 676:95-105, 1996.
Bartolucci, et al., Liquid chromatography tandem mass spectrometric quantitation of sulfamethazine and its metabolites: direct analysis of swine urine by triple quadrupole and by ion trap mass spectrometry, Rapid Commun. Mass Spectrom, 14:967-73 (2000).
Busch, A Glossary for Mass Spectrometry, Mass Spectrometry, 17(65):526-534, 2002.
Capote et al, Identification and determination of fat-soluble vitamins and metabolites in human serum by liquid chromatography/triple quadrupole mass spectrometry with multiple reaction monitoring, Rapid Commun. Mass. Spectrom., 21:1745-1754, 2007.
Coldwell et al, Mass Fragmentographic Assay for 25-Hydroxyvitamin D in Plasma Without Derivatization: Enhanced Sensitivity for Metabolites of Vitamins D2 and D3 After Pre-column Dehydration, Journal of Mass Spectrometry, 30:348-356, (1995).
Coldwell et al, Stable isotope-labeled vitamin D, metabolites and chemical analogs: synthesis and use in mass spectrometric studies, Steroids, 55: 418-432, 1990.
Coldwell et al., Measurement of Vitamins D2 and D3 and Seven Major Metabolites in a Single Sample of Human Plasma Using Gas Chromatography/Mass Spectrometry, Biomedical and Environmental Mass Spectrometry, 16:81-85 (1988).
Extended Search Report dated Feb. 2, 2009 in EP application 06749272.
Extended Search Report dated Dec. 22, 2010 in EP application 08853843.
Guo et al, Steroid profiles using liquid chromatography-Tandem mass spectrometry with atmospheric pressure photoionization source, Arch Pathol Lab Med., 128: 469-475, 2004.
Higashi et al, Characterization of new conjugated metabolites in bile of rats administered 24,25-dihydroxyvitamin D3 and 25-hydroxyvitamin D3, Steroids, 65(5):281-94 (2000).
Higashi et al, Characterization of urinary metabolites of vitamin D3 in man under physiological conditions using liquid chromatography-tandem mass spectrometry, J Pharm Biomed Anal. 29(5):947-55 (2002).

(Continued)

*Primary Examiner* — Jill Warden
*Assistant Examiner* — Monique Cole
(74) *Attorney, Agent, or Firm* — Foley & Lardner LLP

(57) ABSTRACT

Provided are methods of detecting the presence or amount of a dihydroxyvitamin D metabolite in a sample using mass spectrometry. The methods generally comprise ionizing a dihydroxyvitamin D metabolite in a sample and detecting the amount of the ion to determine the presence or amount of the vitamin D metabolite in the sample. In certain preferred embodiments the methods include immunopurifying the dihydroxyvitamin D metabolites prior to mass spectrometry. Also provided are methods to detect the presence or amount of two or more dihydroxyvitamin D metabolites in a single assay.

26 Claims, No Drawings

OTHER PUBLICATIONS

Higashi et al, Liquid chromatography-tandem mass spectrometric method for the determination of salivary 25-hydroxyvitamin D3: a noninvasive tool for the assessment of vitamin D status, Anal. Bioanal Chem, 2008, 391:229-238.

Higashi et al, Simultaneous Determination of 25-Hydroxyvitamin D2 and 25-Hydroxyvitamin D3 in Human Plasma by Liquid Chromatography-Tandem Mass Spectrometry Employing Derivatization with a Cookson-Type Reagent, Biol Pharm Bull., 24(7):738-43, (2001).

International Preliminary Report on Patentability dated Oct. 9, 2007 in application PCT/US2006/012539.

International Preliminary Report on Patentability dated Jun. 1, 2010 in application PCT/US2008/084709.

International Search Report and Written Opinion dated Jan. 26, 2011 in application PCT/US2010/056461.

International Search Report and Written Opinion dated Jan. 27, 2011 in application PCT/US2010/057627.

International Search Report and Written Opinion dated Feb. 7, 2011 in application PCT/US2010/059765.

International Search Report and Written Opinion dated Feb. 8, 2011 in application PCT/US2010/059746.

International Search Report dated Feb. 24, 2009 in application PCT/US2008/084709.

International Search Report dated Jan. 14, 2011 in PCT/US2010/056886.

International Search Report dated Jan. 4, 2007 in application PCT/US2006/012539.

International Search Report dated Feb. 11, 2011 in application PCT/US2010/059771.

Interview Summary dated Jan. 28, 2009 in U.S. Appl. No. 11/101,166.

Jemal, High-throughput quantitative bioanalysis by LC/MS/MS, Biomedical Chromatography, 14:422-429, 2000.

Jones et al, Biological activity of I,25-Dihydroxyvitamin D2 in the Chick, Biochemistry, 15(3): 713-716, 1976.

Jones et al, Current understanding of the molecular actions of Vitamin D, Physiological Reviews, 78(4): 1193-1231, 1998.

Jones et al, Vitamin Ds: Metabolites and Analogs, Chapter 2 in Modern Chromatographic Analysis of Vitamins, Third Edition, 2002, 79 pgs.

Kamao et al, C-3 Epimerization of Vitamin D3 metabolites and further metabolism of C-3 epimers, The Journal of Biological Chemistry, 279 (16):15897-15907, (2004).

Kissmeyer et al, Sensitive analysis of 1a,25-dihydroxyvitamin D3 in biological fluids by liquid chromatography-tandem mass spectrometry, J Chromatogr A., 935(1-2):93-103 (2001).

Kobayashi et al, Tandem immunoaffinity chromatography for plasma 1a,25-dihydroxyvitamin D3 utilizing two antibodies having different specificities: A novel and powerful pretreatment tool for 1a,25-dihydroxyvitamin D3 radioreceptor assays, J.Steroid Biochem. Molec. Biol., 54(5/6): 217-226, 1995.

Kobayashi, et al, Production of a group-specific antibody to 1 alpha,25-dihydroxyvitamin D and its derivatives having the 1 alpha,3 beta-dihydroxylated A-ring structure, Steroids, (1994), 59(7):404-11.

Maunsell et al, Routine Isotope-Dilution Liquid Chromatography-Tandem Mass Spectrometry Assay for Simultaneous Measurement of the 25-Hydroxy Metabolites of Vitamins D2 and D3, Clinical Chemistry, 51:9 1683-1690, (2005).

Merchant et al, Recent advancements in surface-enhanced laser desorption/ionization-time of flight-mass spectrometry, Electrophoresis 21:1164-1177 (2000).

Miller et al, Genetic causes of rickets, Current Opinions in Pediatrics, 11:333-339, 1999.

Odrzywolska et al, Convergent Synthesis, Chiral HPLC, and Vitamin D Receptor Affinity of Analogs of 1,25-Dihydroxycholecalciferol, Chirality, 11:249-255, (1999).

Office Action dated Sep. 29, 2009 for EP Application No. 06749272.8.

Polson et al, Optimization of protein precipitation based upon effectiveness of protein removal and ionization effect in liquid chromatography-tandem mass spectrometry, Journal of Chromatography B, 785:263-275 (2003).

Robb et al, Atmospheric Pressure Photoionization: An Ionization Method for Liquid Chromatography-Mass Spectrometry, Anal. Chem., 72(15): 3653-3659 (2000).

Salm et al, The Quantification of Sirolimus by High-Performance Liquid Chromatography-Tandem Mass Spectrometry and Microparticle Enzyme Immunoassay in Renal Transplant Recipients, Clin. Therapeutics 22 Supl. B:B71-B85 (2000).

Singh et al, C-3 epimers can account for a significant proportion of total circulating 25-hydroxyvitamin D in infants, complicating accurate measurement and interpretation of vitamin D status, The Journal of Clinical Endocrinology & Metabolism, 91(8): 3055-3061, 2006.

Taylor et al, Simultaneous Quantification of Tacrolimus and Sirolimus in Human Blood, by High-Performance Liquid Chromatography—Tandem Mass Spectrometry, Therapeutic Drug Monitoring 22:608-12 (2000).

Tsugawa et al, Determination of 25-hydroxyvitamin D in human plasma using high-performance liquid chromatography-tandem mass spectrometry, Anal. Chem., 77:3001-3007, 2005.

US Notice of Allowance dated Dec. 15, 2009 in U.S. Appl. No. 11/101,166.

US Notice of Allowance dated Mar. 2, 2011 in U.S. Appl. No. 11/386,215.

US Notice of Allowance dated Mar. 3, 2011 in U.S. Appl. No. 11/946,765.

US Notice of Allowance dated May 20, 2011 in U.S. Appl. No. 12/630,790.

US Notice of Allowance dated Aug. 19, 2009 for U.S. App. No. 11/101,166.

US Office Action dated Apr. 12, 2010 in U.S. Appl. No. 11/386,215.
US Office Action dated Jan. 6, 2011 in U.S. Appl. No. 12/630,790.
US Office Action dated Oct. 8, 2008 in U.S. Appl. No. 11/101,166.
US Office Action dated Oct. 5, 2010 in U.S. Appl. No. 11/386,215.
US Office Action dated Dec. 17, 2010 in U.S. Appl. No. 11/946,765.
US Office Action dated Dec. 17, 2010 in U.S. Appl. No. 12/630,796.
US Office Action dated Jun. 24, 2010 in U.S. Appl. No. 11/946,765.
US Office Action dated Jun. 28, 2010 in U.S. Appl. No. 12/630,790.
US Office Action dated Jul. 7, 2010 in U.S. Appl. No. 12/630,796.

Vieth et al, Age-related changes in the 25-hydroxyvitamin D versus parathyroid hormone relationship suggest a different reason why older adults require more Vitamin D, The Journal of Clinical Endocrinology & Metabolism, 88(1): 185-191, 2003.

Vieth, Vitamin D supplementation, 25-hydroxyvitamin D concentrations, and safety, Am J Clin Nutr, 69:842-856, 1999.

Vogeser et al, Candidate reference method for the quantification of circulating 25-Hydroxyvitamin D3 by liquid chromatography-tandem mass spectrometry, Clinical Chemistry, 50(8): 1415-1417, (2004).

Vreeken et al, On-line post-column Diels-Alder derivatization for the determination of vitamin D3 and its metabolites by liquid chromatography/thermospray mass spectromety, Biological Mass Spectrometry, 22:621-632, (1993).

Watson et al, Analysis of Vitamin D and its metabolites using thermospray liquid chromatography/Mass spectrometry, Biomedical Chromatography, 5:153-160, 1991.

Wharton et al, Rickets. The Lancet, 362: 1389-1400, 2003.

Wright et al, Proteinchip surface enhanced laser desorption/ionization (SELDI) mass spectrometry: a novel protein biochip technology for detection of prostate cancer biomarkers in complex protein mixtures, Prostatic Cancer and Prostatic Diseases, 2:264-76, (1999).

Yeung et al, Characterization of the Metabolic Pathway of 1,25-Dihydroxy-16-Ene Vitamin D3 in Rat Kidney By On-Line High Performance Liquid Chromatography-Electrospray Tandem Mass Spectrometry, Biochemical Pharmacology, vol. 49, No. 8, pp. 1099-1110, (1995).

Yeung et al, Characterization of vitamin D3 metabolites using continuous-flow fast atom bombardment tandem mass spectrometry and high performance liquid chromatography Chromatogr, 645(1):115-123(1993).

Yeung, et al, The role of mass spectrometry in vitamin D research, Mass Spec Reviews, (1995), 14(3):179-194.

Zimmer et al, Comparison of turbulent-flow chromatography with automated solid-phase extraction in 96-well plates and liquid-liquid extraction used as plasma sample preparation techniques for liquid chromatography-tandem mass spectromety, J. Chromatogr. A 854:23-35 (1999).

US Office Action dated Jun. 29, 2011 in U.S. Appl. No. 13/115,935.

US Notice of Allowance dated Jul. 6, 2011 in U.S. Appl. No. 12/630,796.

US Office Action dated Jul. 21, 2011 in U.S. Appl. No. 13/165,685.

US Office Action dated Jul. 29, 2011 in U.S. Appl. No. 13/117,997.

US Office Action dated Aug. 4, 2011 in U.S. Appl. No. 13/115,916.

US Notice of Allowance dated Aug. 4, 2011 in U.S. Appl. No. 13/115,935.

US Notice of Allowance dated Aug. 24, 2011 in U.S. Appl. No. 13/165,685.

US Notice of Allowance dated Sep. 16, 2011 in U.S. Appl. No. 13/115,916.

Examination Report dated Sep. 20, 2011 for EP Application No. 08 853 843.4.

\* cited by examiner

METHODS FOR DETECTING DIHYDROXYVITAMIN D METABOLITES BY MASS SPECTROMETRY

CROSS REFERENCE TO RELATED PATENT APPLICATIONS

This application claims priority under 35 U.S.C. §120 to U.S. application Ser. No. 11/946,765, filed Nov. 28, 2007, incorporated herein by reference in its entirety.

FIELD OF THE INVENTION

The invention relates to the detection of dihydroxyvitamin D metabolites. In a particular aspect, the invention relates to methods for detecting vitamin D metabolites by mass spectrometry.

BACKGROUND OF THE INVENTION

Vitamin D is an essential nutrient with important physiological roles in the positive regulation of calcium ($Ca^{2+}$) homeostasis. Vitamin D can be made de novo in the skin by exposure to sunlight or it can be absorbed from the diet. There are two forms of vitamin D; vitamin $D_2$ (ergocalciferol) and vitamin $D_3$ (cholecalciferol). Vitamin $D_3$ is the form synthesized de novo by animals. It is also a common supplement added to milk products and certain food products produced in the United States. Both dietary and intrinsically synthesized vitamin $D_3$ must undergo metabolic activation to generate bioactive metabolites. In humans, the initial step of vitamin $D_3$ activation occurs primarily in the liver and involves hydroxylation to form the intermediate metabolite 25-hydroxyvitamin $D_3$ (25-hydroxycholecalciferol; calcifediol; $25OHD_3$). Calcifediol is the major form of vitamin $D_3$ in the circulation. Circulating $25OHD_3$ is then converted by the kidney to 1,25-dihydroxyvitamin $D_3$ (calcitriol; $1,25(OH)_2D_3$), which is generally believed to be the metabolite of vitamin $D_3$ with the highest biological activity.

Vitamin $D_2$ is derived from fungal and plant sources. Some over-the-counter dietary supplements contain ergocalciferol (vitamin $D_2$) rather than cholecalciferol (vitamin $D_3$). Drisdol, the only high-potency prescription form of vitamin D available in the United States, is formulated with ergocalciferol. Vitamin $D_2$ undergoes a similar pathway of metabolic activation in humans as vitamin $D_3$, forming the metabolites 25-hydroxyvitamin $D_2$ ($25OHD_2$) and 1,25-dihydroxyvitamin $D_3$ ($1,25(OH)_2D_2$). Vitamin $D_2$ and vitamin $D_3$ have long been assumed to be biologically equivalent in humans, however recent reports suggest that there may be differences in the bioactivity and bioavailability of these two forms of vitamin D (Armas et. al., (2004) J. Clin. Endocrinol. Metab. 89:5387-5391).

Measurement of vitamin D, the inactive vitamin D precursor, is rare in clinical settings and has little diagnostic value. Rather, serum levels of 25-hydroxyvitamin $D_3$ and 25-hydroxyvitamin $D_2$ (total 25-hydroxyvitamin D; "25OHD") are a useful index of vitamin D nutritional status and the efficacy of certain vitamin D analogs. Therefore, the measurement of 25OHD is commonly used in the diagnosis and management of disorders of calcium metabolism. In this respect, low levels of 25OHD are indicative of vitamin D deficiency associated with diseases such as hypocalcemia, hypophosphatemia, secondary hyperparathyroidism, elevated alkaline phosphatase, osteomalacia in adults and rickets in children. In patients suspected of vitamin D intoxication, elevated levels of 25OHD distinguishes this disorder from other disorders that cause hypercalcemia.

Measurement of $1,25(OH)_2D$ is also used in clinical settings. For example certain disease states such as kidney failure can be diagnosed by reduced levels of circulating $1,25(OH)_2D$ and elevated levels of $1,25(OH)_2D$ may be indicative of excess parathyroid hormone or may be indicative of certain diseases such as sarcoidosis or certain types of lymphoma.

Detection of vitamin D metabolites has been accomplished by radioimmunoassay with antibodies co-specific for 25-hydroxyvitamin $D_3$ and 25-hydroxyvitamin $D_2$. Because the current immunologically-based assays do not separately resolve 25-hydroxyvitamin $D_3$ and 25-hydroxyvitamin $D_2$, the source of a deficiency in vitamin D nutrition cannot be determined without resorting to other tests. More recently, reports have been published that disclose methods for detecting specific vitamin D metabolites using mass spectrometry. For example Yeung B, et al., J Chromatogr. 1993, 645(1):115-23; Higashi T, et al., Steroids. 2000, 65(5):281-94; Higashi T, et al., Biol Pharm Bull. 2001, 24(7):738-43; and Higashi T, et al., J Pharm Biomed Anal. 2002, 29(5):947-55 disclose methods for detecting various vitamin D metabolites using liquid chromatography and mass spectrometry. These methods require that the metabolites be derivatized prior to detection by mass-spectrometry. Methods to detect underivatized 1,25 $(OH)_2D_3$ by liquid chromatography mass-spectrometry are disclosed in Kissmeyer and Sonne, J Chromatogr A. 2001, 935(1-2):93-103.

SUMMARY OF THE INVENTION

The present invention provides methods for detecting the presence or amount of a dihydroxyvitamin D metabolite in a sample by mass spectrometry, including tandem mass spectrometry.

In one aspect, methods are provided for determining the presence or amount of one or more dihydroxyvitamin D metabolites by tandem mass spectrometry, that include: (a) immunopurifying one or more dihydroxyvitamin D metabolites from the sample; (b) further purifying the immunopurified dihydroxyvitamin D metabolite(s) by HPLC; (c) determining the amount of the vitamin D metabolites obtained from step (b) by tandem mass spectrometry by: (i) generating a precursor ion of the dihydroxyvitamin D metabolite(s); (ii) generating one or more fragment ions of the precursor ion; and (iii) detecting the presence or amount of one or more of the ions generated in step (c) or (d) or both and relating the detected ions to the presence or amount of the dihydroxyvitamin D metabolite(s) in the sample. In certain preferred embodiments, dihydroxyvitamin D metabolites are immunopurified from the sample using anti-dihydroxyvitamin D antibodies attached to a solid support; preferably the dihydroxyvitamin D metabolites are immunopurified using immunoparticles; preferably the immunoparticles have anti-dihydroxyvitamin D antibodies on their surface. In certain embodiments, the dihydroxyvitamin D metabolite(s) include $1\alpha,25(OH)_2D_2$; in certain embodiments the dihydroxyvitamin D metabolite(s) include $1\alpha,25(OH)_2D_3$; in some particularly preferred embodiments, provided are methods for determining the presence or amount of $1\alpha,25(OH)_2D_2$ and $1\alpha,25 (OH)_2D_3$ in a single assay.

In certain preferred embodiments of the above aspect, the dihydroxyvitamin D metabolite(s) are derivatized prior to mass spectrometry; in some particularly preferred embodiments the dihydroxyvitamin D metabolite(s) are derivatized with a Cookson-type reagent (e.g., a 4-substituted 1,2,4-triazoline-3,5-dione; TAD); in certain particularly preferred embodiments the dihydroxyvitamin D metabolite(s) are derivatized with 4-phenyl-1,2,4-triazoline-3,5-dione (PTAD); and in yet other particularly preferred embodiments the dihydroxyvitamin D metabolite(s) are derivatized with 4'-carboxyphenyl-TAD. In certain preferred embodiments the dihydroxyvitamin D metabolite(s) include $1\alpha,25(OH)_2 D_2$; the $1\alpha,25(OH)_2D_2$ is derivatized with 4-phenyl-1,2,4-triazoline-3,5-dione (PTAD) prior to mass spectrometry; and more preferably the precursor ion of $1\alpha,25(OH)_2D_2$ has a mass/charge ratio of 586.37±0.5. In certain preferred embodiments the dihydroxyvitamin D metabolite(s) include $1\alpha,25(OH)_2D_3$; the $1\alpha,25(OH)_2D_3$ is derivatized with 4-phenyl-1,2,4-triazoline-3,5-dione (PTAD) prior to mass spectrometry; and more preferably the precursor ion of $1\alpha,25(OH)_2D_3$ has a mass/charge ratio of 574.37±0.5. In certain preferred embodiments, the dihydroxyvitamin D metabolite(s) are derivatized with 4-phenyl-1,2,4-triazoline-3,5-dione (PTAD) prior to mass spectrometry and the fragment ions include at least one ion having a mass/charge ratio of 314.12±0.5

In some preferred embodiments the dihydroxyvitamin D metabolite(s) are not derivatized prior to mass spectrometry. In certain particularly preferred embodiments the dihydroxyvitamin D metabolite(s) include $1\alpha,25(OH)_2D_2$, the $1\alpha,25(OH)_2D_2$ is not derivatized prior to mass spectrometry and more preferably the precursor ion of the non-derivatized $1\alpha,25(OH)_2D_2$ has a mass/charge ratio of 411.35±0.5. In certain particularly preferred embodiments the dihydroxyvitamin D metabolite(s) include $1\alpha,25(OH)_2D_3$, the $1\alpha,25(OH)_2D_3$ is not derivatized prior to mass spectrometry and more preferably the precursor ion of the non-derivatized $1\alpha,25(OH)_2D_3$ has a mass/charge ratio of 399.35±0.5. In certain particularly preferred embodiments, the dihydroxyvitamin D metabolite(s) are not derivatized and the fragment ions include one or more ions selected from the group consisting of ions having a mass/charge ratio of 151.12±0.5 and 135.12±0.5.

In particularly preferred embodiments, methods are provided for determining the amount of $1\alpha,25(OH)_2D_2$ and $1\alpha,25(OH)_2D_3$ in a human body sample by tandem mass spectrometry in a single assay that include: (a) immunopurifying the $1\alpha,25(OH)_2D_2$ and $1\alpha,25(OH)_2D_3$ from the sample; (b) derivatizing the $1\alpha,25(OH)_2D_2$ and $1\alpha,25(OH)_2D_3$ with 4-phenyl-1,2,4-triazoline-3,5-dione (PTAD); (c) purifying the derivatized $1\alpha,25(OH)_2D_2$ and $1\alpha,25(OH)_2D_3$ from step (b) by HPLC; (d) determining the amount of $1\alpha,25(OH)_2D_2$ and $1\alpha,25(OH)_2D_3$ obtained from step (c) by tandem mass spectrometry by; (i) generating a precursor ion of the derivatized $1\alpha,25(OH)_2D_2$ having a mass/charge ratio of 586.37±0.5 and a precursor ion of the derivatized $1\alpha,25(OH)_2 D_3$ having a mass/charge ratio of 574.37±0.5; (ii) generating one or more fragment ions of the precursor ions from step (i) wherein at least one of the fragment ions have a mass charge ration of 314.12±0.5; and (iii) detecting the presence or amount of one or more of the ions generated in step (i) or (ii) or both and relating the detected ions to the presence or amount of $1\alpha,25(OH)_2D_2$ and $1\alpha,25(OH)_2D_3$ in the sample.

As used herein, the term "dihydroxyvitamin D metabolite" refers to any dihydroxylated vitamin D species that may be found in the circulation of an animal which is formed by a biosynthetic or metabolic pathway for vitamin D or a synthetic vitamin D analog. Preferably the dihydroxyvitamin D metabolite is hydroxylated at the 1 and 25 position. In particularly preferred embodiments, the vitamin D metabolite is $1\alpha,25$-dihydroxyvitamin $D_3$ ($1\alpha,25(OH)_2D_3$) or $1\alpha,25$-dihydroxyvitamin $D_2$ ($1\alpha,25(OH)_2D_2$). In certain preferred embodiments the dihydroxyvitamin D metabolites are naturally present in a body fluid of a mammal, more preferably a human. In certain particularly preferred embodiments, the methods as described herein detect $1\alpha,25$-dihydroxyvitamin $D_3$ ($1\alpha,25(OH)_2D_3$) and/or $1\alpha,25$-dihydroxyvitamin ($1\alpha,25(OH)_2D_2$) and do not detect one or more dihydroxyvitamin-D metabolites selected from the group consisting of 24,25-dihydroxyvitamin D; 25,26-dihydroxyvitamin D; and $1\alpha,3\alpha$-dihydroxyvitamin D.

As used herein, the term "purification" or "purify" refers to a procedure that enriches the amount of one or more analytes of interest relative to one or more other components of the sample. Purification, as used herein does not require the isolation of an analyte from all others. In preferred embodiments, a purification step or procedure can be used to remove one or more interfering substances, e.g. one or more substances that would interfere with the operation of the instruments used in the methods or substances that may interfere with the detection of an analyte ion by mass spectrometry.

As used herein, the term "immunopurification" or "immunopurify" refers to a purification procedure that utilizes antibodies, including polyclonal or monoclonal antibodies, to enrich the one or more analytes of interest. Immunopurification can be performed using any of the immunopurification methods well known in the art. Often the immunopurification procedure utilizes antibodies bound, conjugated or otherwise attached to a solid support, for example a column, well, tube, gel, capsule, particle or the like. Immunopurification as used herein includes without limitation procedures often referred to in the art as immunoprecipitation, as well as procedures often referred to in the art as affinity chromatography.

As used herein, the term "immunoparticle" refers to a capsule, bead, gel particle or the like that has antibodies bound, conjugated or otherwise attached to its surface (either on and/or in the particle). In certain preferred embodiments, immunoparticles are sepharose or agarose beads. In alternative preferred embodiments, immunoparticles are glass, plastic or silica beads, or silica gel.

As used herein, the term "anti-dihydroxyvitamin D antibody" refers to any polyclonal or monoclonal antibody that has an affinity for one or more dihydroxyvitamin D metabolites. In certain preferred embodiments the anti-dihydroxyvitamin D antibodies bind $1\alpha,25(OH)_2D_3$ and $1\alpha,25(OH)_2D_2$. In some preferred embodiments the anti-dihydroxyvitamin D antibodies bind $1\alpha,25(OH)_2D_3$ and $1\alpha,25(OH)_2D_2$ with equal or similar affinity. In other preferred embodiments the anti-dihydroxyvitamin D antibodies bind $1\alpha,25(OH)_2D_3$ with significantly higher affinity than $1\alpha,25(OH)_2D_2$; in alternative preferred embodiments the anti-dihydroxyvitamin D antibodies bind $1\alpha,25(OH)_2D_2$ with significantly higher affinity than $1\alpha,25(OH)_2D_3$. In various embodiments the specificity of anti-dihydroxyvitamin D antibodies to chemical species other than dihydroxyvitamin D metabolites may vary; for example in certain preferred embodiments the anti-dihydroxyvitamin D antibodies are specific for dihydroxyvitamin D metabolites and thus have little or no affinity for chemical species other than dihydroxyvitamin D metabolites (e.g., other vitamin D metabolites such as vitamin D or 25-hydroxyvitamin D), whereas in other preferred embodiments the anti-dihydroxyvitamin D antibodies are non-specific and thus bind certain chemical species other than dihydroxyvitamin D metabolites (for example a non-specific anti-dihydroxyvitamin D antibody may bind other vitamin D metabolites such as vitamin D or 25-hydroxyvitamin D).

In some preferred embodiments of the methods disclosed herein, the dihydroxyvitamin D metabolite(s) are not derivatized prior to mass spectrometry. In other preferred embodiments, the vitamin D metabolites are derivatized prior to mass spectrometry.

As used herein, "biological sample" refers to any sample from a biological source. As used herein, "body fluid" means any fluid that can be isolated from the body of an individual. For example, "body fluid" may include blood, plasma, serum, bile, saliva, urine, tears, perspiration, and the like.

As used herein, "derivatizing" means reacting two molecules to form a new molecule. Derivatizing agents may include Cookson-type reagents (e.g., 4-substituted 1,2,4-triazoline-3,5-diones; TAD); isothiocyanate groups, dinitrofluorophenyl groups, nitrophenoxycarbonyl groups, and/or phthalaldehyde groups. In certain preferred embodiments, derivitization is performed using methods such as those disclosed in, for example, Vreeken, et. al., Biol. Mass Spec. 22:621-632; Yeung B, et al., J Chromatogr. 1993, 645(1):115-23; Higashi T, et al., Biol Pharm Bull. 2001, 24(7):738-43; or Higashi T, et al., J Pharm Biomed Anal. 2002, 29(5):947-55. In preferred embodiments the derivatizing agents are Cookson-type reagents. Particularly preferred derivatizing reagents include 4-phenyl-1,2,4-triazoline-3,5-dione (PTAD); 4'-carboxyphenyl-TAD; 4-[4-(6-methoxy-2-benzoxazolyl)phenyl]-1,2,4-triazoline-3,5-dione (MBOTAD).; 4-[2-(6,7-dimethoxy-4-methyl-3-oxo-3,4-ihydroquinoxalyl)ethyl]-1,2,4-triazoline-3,5-dione (DMEQTAD); 4-nitrophenyl-TAD; 4-pentafluorophenyl-TAD; 4-ferrocenylethyl-TAD; 4-quarternaryamine-TAD; and the like. In certain preferred embodiments derivitization is performed prior to chromatography; however in other preferred embodiments derivitization is performed after chromatography, for example using methods similar to those described in Vreeken, et. al., Biol. Mass Spec. 22:621-632.

As used herein, "chromatography" refers to a process in which a chemical mixture carried by a liquid or gas is separated into components as a result of differential distribution of the chemical entities as they flow around or over a stationary liquid or solid phase.

As used herein, "liquid chromatography" (LC) means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). "Liquid chromatography" includes reverse phase liquid chromatography (RPLC), high performance liquid chromatography (HPLC) and high turbulence liquid chromatography (HTLC).

As used herein, the term "HPLC" or "high performance liquid chromatography" refers to liquid chromatography in which the degree of separation is increased by forcing the mobile phase under pressure through a stationary phase, typically a densely packed column.

As used herein, the term "gas chromatography" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase As used herein, "mass spectrometry" (MS) refers to an analytical technique to identify compounds by their mass. MS technology generally includes (1) ionizing the compounds to form charged compounds; and (2) detecting the molecular weight of the charged compound and calculating a mass-to-charge ratio (m/z). The compound may be ionized and detected by any suitable means. A "mass spectrometer" generally includes an ionizer and an ion detector. See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 2:264-76 (1999); and Merchant and Weinberger, *Electrophoresis* 21:1164-67 (2000).

The term "electron ionization" as used herein refers to methods in which an analyte of interest in a gaseous or vapor phase interacts with a flow of electrons. Impact of the electrons with the analyte produces analyte ions, which may then be subjected to a mass spectrometry technique.

The term "chemical ionization" as used herein refers to methods in which a reagent gas (e.g. ammonia) is subjected to electron impact, and analyte ions are formed by the interaction of reagent gas ions and analyte molecules.

The term "fast atom bombardment" as used herein refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine.

The term "field desorption" as used herein refers to methods in which a non-volatile test sample is placed on an ionization surface, and an intense electric field is used to generate analyte ions.

The term "ionization" as used herein refers to the process of generating an analyte ion having a net electrical charge equal to one or more electron units. Negative ions are those having a net negative charge of one or more electron units, while positive ions are those having a net positive charge of one or more electron units.

The term "operating in negative ion mode" refers to those mass spectrometry methods where negative ions are detected. Similarly, "operating in positive ion mode" refers to those mass spectrometry methods where positive ions are detected.

The term "desorption" as used herein refers to the removal of an analyte from a surface and/or the entry of an analyte into a gaseous phase.

In a second aspect, methods are provided for determining the presence or amount of $1\alpha,25(OH)_2D_2$ in a sample by tandem mass spectrometry that include (a) derivatizing the $1\alpha,25(OH)_2D_2$ in the sample with 4-phenyl-1,2,4-triazoline-3,5-dione (PTAD); (b) purifying the derivatized $1\alpha,25(OH)_2D_2$ by HPLC; (c) generating a precursor ion of the derivatized $1\alpha,25(OH)_2D_2$ having a mass/charge ratio of 586.37±0.5; (d) generating one or more fragment ions of the precursor ion, wherein at least one of the fragment ions comprise an ion having a mass/charge ratio of 314.12±0.5; and (e) detecting the presence or amount of one or more of the ions generated in step (c) or (d) or both and relating the detected ions to the presence or amount of $1\alpha,25(OH)_2D_2$ in the sample. In certain preferred embodiments the $1\alpha,25(OH)_2D_2$ in the sample is purified by immunopurification prior to step (a); preferably the immunopurification includes immunopurification with immunoparticles; preferably the immunoparticles have an anti-dihydroxyvitamin D metabolite antibody bound to the surface. In some preferred embodiments of this aspect, the method further includes determining the presence or amount of $1\alpha,25(OH)_2D_3$ in the sample; preferably the $1\alpha,25(OH)_2D_3$ is derivatized with 4-phenyl-1,2,4-triazoline-3,5-dione (PTAD) prior to mass spectrometry; more preferably the precursor ion of the 1α,25(OH)$_2$D$_3$ has a mass/charge ratio of 574.37±0.5

In a third aspect, methods are provided for determining the presence or amount of 1α,25(OH)$_2$D$_3$ in a sample by tandem mass spectrometry that include (a) derivatizing the 1α,25(OH)$_2$D$_3$ in the sample with 4-phenyl-1,2,4-triazoline-3,5-dione (PTAD); (b) purifying the derivatized 1α,25(OH)$_2$D$_3$ by HPLC; (c) generating a precursor ion of the derivatized 1α,25(OH)$_2$D$_3$ having a mass/charge ratio of 574.37±0.5; (d) generating one or more fragment ions of the precursor ion, wherein at least one of the fragment ions comprise an ion having a mass/charge ratio of 314.12±0.5; and (e) detecting the presence or amount of one or more of the ions generated in step (c) or (d) or both and relating the detected ions to the presence or amount of 1α,25(OH)$_2$D$_3$ in the sample. In certain preferred embodiments the 1α,25(OH)$_2$D$_3$ in the sample is purified by immunopurification prior to step (a); preferably the immunopurification includes immunopurification with immunoparticles; preferably the immunoparticles have an anti-dihydroxyvitamin D metabolite antibody bound to the surface. In some preferred embodiments of this aspect, the method further includes determining the presence or amount of 1α,25(OH)$_2$D$_2$ in the sample; preferably the 1α,25(OH)$_2$D$_2$ is derivatized with 4-phenyl-1,2,4-triazoline-3,5-dione (PTAD) prior to mass spectrometry; more preferably the precursor ion of the 1α,25(OH)$_2$D$_2$ has a mass/charge ratio of 586.37±0.5.

In a fourth aspect, methods are provided for determining the presence or amount of 1α,25(OH)$_2$D$_2$ in a sample by tandem mass spectrometry that include (a) purifying the 1α,25(OH)$_2$D$_2$ by HPLC; (b) generating a precursor ion of the 1α,25(OH)$_2$D$_2$ having a mass/charge ratio of 411.35±0.5; (c) generating one or more fragment ions of the precursor ion, wherein the fragment ions include one or more ions selected from the group consisting of ions having a mass/charge ratio of 151.12±0.5 and 135.12±0.5; and (d) detecting the presence or amount of one or more of the ions generated in step (b) or (c) or both and relating the detected ions to the presence or amount of the 1α,25(OH)$_2$D$_2$ in the sample. In preferred embodiments of this aspect the 1α,25(OH)$_2$D$_2$ is not derivatized prior to mass spectrometry. In certain preferred embodiments the 1α,25(OH)$_2$D$_2$ in the sample is purified by immunopurification prior to step (a); preferably the immunopurification includes immunopurification with immunoparticles; preferably the immunoparticles have an anti-dihydroxyvitamin D metabolite antibody bound to the surface. In some preferred embodiments of this aspect, the method further includes determining the presence or amount of 1α,25(OH)$_2$D$_3$ in the sample; preferably the 1α,25(OH)$_2$D$_3$ is not derivatized prior to mass spectrometry; more preferably the precursor ion of the 1α,25(OH)$_2$D$_3$ has a mass/charge ratio of 399.35±0.5.

In a fifth aspect, methods are provided for determining the presence or amount of 1α,25(OH)$_2$D$_3$ in a sample by tandem mass spectrometry that include (a) purifying the 1α,25(OH)$_2$D$_3$ by HPLC; (b) generating a precursor ion of the 1α,25(OH)$_2$D$_3$ having a mass/charge ratio of 399.35±0.5; (c) generating one or more fragment ions of the precursor ion, wherein the fragment ions include one or more ions selected from the group consisting of ions having a mass/charge ratio of 151.12±0.5 and 135.12±0.5; and (d) detecting the presence or amount of one or more of the ions generated in step (b) or (c) or both and relating the detected ions to the presence or amount of the 1α,25(OH)$_2$D$_3$ in the sample. In preferred embodiments of this aspect the 1α,25(OH)$_2$D$_3$ is not derivatized prior to mass spectrometry. In certain preferred embodiments the 1α,25(OH)$_2$D$_3$ in the sample is purified by immunopurification prior to step (a); preferably the immunopurification includes immunopurification with immunoparticles; preferably the immunoparticles have an anti-dihydroxyvitamin D metabolite antibody bound to the surface. In some preferred embodiments of this aspect, the method further includes determining the presence or amount of 1α,25(OH)$_2$D$_2$ in the sample; preferably the 1α,25(OH)$_2$D$_2$ is not derivatized prior to mass spectrometry; more preferably the precursor ion of the 1α,25(OH)$_2$D$_2$ has a mass/charge ratio of 411.35±0.5.

The term "about" as used herein in reference to quantitative measurements, refers to the indicated value plus or minus 10%.

DETAILED DESCRIPTION OF THE INVENTION

Methods are described for detecting and quantifying dihydroxyvitamin D metabolites in a test sample. Some preferred methods disclosed herein utilize liquid chromatography (LC), most preferably HPLC, to purify selected analytes, and combine this purification with unique methods of mass spectrometry (MS), thereby providing a high-throughput assay system for detecting and quantifying dihydroxyvitamin D metabolites in a test sample. In certain particularly preferred embodiments, dihydroxyvitamin D metabolites are immunopurified prior to mass spectrometry. The preferred embodiments are particularly well suited for application in large clinical laboratories. Methods of detecting and quantifying dihydroxyvitamin D metabolites are provided that have enhanced specificity and are accomplished in less time and with less sample preparation than required in other dihydroxyvitamin D metabolite assays.

Suitable test samples include any test sample that may contain the analyte of interest. For example, samples obtained during the manufacture of an analyte can be analyzed to determine the composition and yield of the manufacturing process. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably humans. Particularly preferred samples include blood, plasma, serum, hair, muscle, urine, saliva, tear, cerebrospinal fluid, or other tissue sample. Such samples may be obtained, for example, from a patient; that is, a living person presenting oneself in a clinical setting for diagnosis, prognosis, or treatment of a disease or condition. The test sample is preferably obtained from a patient, for example, blood serum.

Sample Preparation for Mass Spectrometry

Methods may be used prior to mass spectrometry to enrich dihydroxyvitamin D metabolites relative to other components in the sample, or to increase the concentration of the dihydroxyvitamin D metabolites in the sample. Such methods include, for example, filtration, centrifugation, thin layer chromatography (TLC), electrophoresis including capillary electrophoresis, affinity separations including immunoaffinity separations, extraction methods including ethyl acetate extraction and methanol extraction, and the use of chaotropic agents or any combination of the above or the like.

Samples may be processed or purified to obtain preparations that are suitable for analysis by mass spectrometry. Such purification will usually include chromatography, such as liquid chromatography, and may also often involve an additional purification procedure that is performed prior to chromatography. Various procedures may be used for this purpose depending on the type of sample or the type of chromatography. Examples include filtration, extraction, precipitation, centrifugation, delipidization, dilution, combinations thereof and the like. Protein precipitation is one preferred method of preparing a liquid biological sample, such as serum or plasma, for chromatography. Such protein purification methods are well known in the art, for example. Polson et al., *Journal of Chromatography B* 785:263-275 (2003), describes protein precipitation methods suitable for use in the methods of the invention. Protein precipitation may be used to remove most of the protein from the sample leaving dihydroxyvitamin D metabolites soluble in the supernatant. The samples can be centrifuged to separate the liquid supernatant from the precipitated proteins. The resultant supernatant can then be applied to liquid chromatography and subsequent mass spectrometry analysis. In one embodiment of the invention, the protein precipitation involves adding one volume of the liquid sample (e.g. plasma) to about four volumes of methanol. In certain embodiments, the use of protein precipitation obviates the need for high turbulence liquid chromatography ("HTLC") or on-line extraction prior to HPLC and mass spectrometry. Accordingly in such embodiments, the method involves (1) performing a protein precipitation of the sample of interest; and (2) loading the supernatant directly onto the HPLC-mass spectrometer without using on-line extraction or high turbulence liquid chromatography ("HTLC").

Immunopurification.

In particularly preferred embodiments, the methods include immunopurifying dihydroxyvitamin D metabolites prior to mass spectrometry analysis. The immunopurification step may be performed using any of the immunopurification methods well known in the art. Often the immunopurification procedure utilizes antibodies bound, conjugated, immobilized or otherwise attached to a solid support, for example a column, well, tube, capsule, particle or the like. Generally, immunopurification methods involve (1) incubating a sample containing the analyte of interest with antibodies such that the analyte binds to the antibodies, (2) performing one or more washing steps, and (3) eluting the analyte from the antibodies.

In certain embodiments the incubation step of the immunopurification is performed with the antibodies free in solution and the antibodies are subsequently bound or attached to a solid surface prior to the washing steps. In certain embodiments this can be achieved using a primary antibody that is an anti-dihydroxyvitamin D antibody and a secondary antibody attached to a solid surface that has an affinity to the primary anti-dihydroxyvitamin D antibody. In alternative embodiments, the primary antibody is bound to the solid surface prior to the incubation step.

Appropriate solid supports include without limitation tubes, slides, columns, beads, capsules, particles, gels, and the like. In some preferred embodiments, the solid support is a multi-well plate, such as, for example, a 96 well plate, a 384-well plate or the like. In certain preferred embodiments the solid support are sephararose or agarose beads or gels. There are numerous methods well known in the art by which antibodies (for example, an anti-dihydroxyvitamin D antibody or a secondary antibody) may be bound, attached, immobilized or coupled to a solid support, e.g., covalent or non-covalent linkages adsorption, affinity binding, ionic linkages and the like. In certain preferred embodiments antibodies are coupled using CNBr, for example the antibodies may be coupled to CNBr activated sepharose. In other embodiments, the antibody is attached to the solid support through an antibody binding protein such as protein A, protein G, protein A/G, or protein L.

The washing step of the immunopurification methods generally involve washing the solid support such that the dihydroxyvitamin D metabolites remain bound to the anti-dihydroxyvitamin D antibodies on the solid support. The elution step of the immunopurification generally involves the addition of a solution that disrupts the binding of dihydroxyvitamin D metabolites to the anti-dihydroxyvitamin D antibodies. Exemplary elution solutions include organic solutions (preferably ethanol), salt solutions, and high or low pH solutions.

In certain preferred embodiments, immunopurification is performed using immunoparticles having anti-dihydroxyvitamin D antibodies. In certain preferred embodiments the test sample possibly containing dihydroxyvitamin D metabolites and the immunoparticles are mixed in a tube for incubation and binding of dihydroxyvitamin D metabolites to the anti-dihydroxyvitamin D antibodies attached to the immunoparticles; the tube is centrifuged leaving the immunoparticles in a pellet; the supernatant is removed; the immunoparticles are washed one or more times by adding a solution to the pellet and recentrifuging; and the dihydroxyvitamin D metabolites are eluted by adding an elution solution to the immunoparticles, the tube is centrifuged leaving the immunoparticles in a pellet; and the supernatant containing dihydroxyvitamin D metabolites is collected. In related preferred embodiments, the immunopurification is performed using a column or cartridge that contains immunoparticles having anti-dihydroxyvitamin D antibodies. Preferably, the such column or cartridge is configured and arranged in a manner to allow solutions to flow through while keeping the immunoparticles contained therein. In certain preferred embodiments, the solution is forced through the column or cartridge by gravity, centrifugation or pressure. The use of columns may improve the ease of performing the incubation, washing and elution steps. In some preferred embodiments, the immunopurification is performed by affinity chromatography; preferably automated affinity chromatography; preferably affinity-HPLC; or preferably affinity chromatography using an automated system such as the AKTA FPLC Chromatographic system sold commercially by GE Healthcare (formerly Amersham biosciences).

In certain embodiments, the sample preparation and immunopurification can be performed using methods and reagents from commercially available kits. For example, IDS Inc (Fountain Hills, Ariz.) offers a 1,25-Dihydroxy Vitamin D $^{125}$I Radioimmunoassay kit (Catalogue Number AA-54F1) that includes directions and reagents for extracting and immunoextracting dihydroxyvitamin D prior to the radioimmunoassay (RIA). See the "Product Support" document for the Catalogue Number AA-54F1 IDS, Inc., kit which is hereby incorporated by reference in its entirety. In particular, the IDS dihydroxyvitamin D RIA kit includes a dextran sulphate/magnesium chloride delipidization step and an immunoextraction step using an immunocapsule device containing a suspension of particles to which is attached a monoclonal antibody specific for 1,25 dihydroxyvitamin D. Accordingly, in certain embodiments of the methods described herein, the samples are subject to vitamin D immunopurification using the IDS kit or methods, reagents and dihydroxyvitamin D immunopurification devices similar to those provided in the IDS kit. Antibodies and dihydroxy purification immunopurification devices are also provided with the 1,25-(OH)2-Vitamin D ImmunoTube ELISA Kit (Catalog Number 30-2113) offered commercially by ALPO Diagnostics (Salem, N.H.). The kit includes an anti 1,25-(OH)$_2$ vitamin-D detection antibody (Catalog number K2113A1), ImmunoTube columns for immunopurification of 1,25-dihydroxyvitamin D (Catalog Number K2113.SI) as well as buffers and other reagents that may be used to immunopurify 1,25-dihydroxyvitamin D. In certain embodiments of the methods described herein, one or more of the components of the ALPO Diagnostics kit are used in to immunopurify 1,25-dihydroxyvitamin D.

Liquid Chromatography.

Generally, chromatography is performed prior to mass spectrometry, preferably the chromatography is liquid chromatography, more preferably high performance liquid chromatography (HPLC). In some preferred embodiments the chromatography is not gas chromatography. Preferably, the methods of the invention are performed without subjecting the samples, or the dihydroxyvitamin D metabolites of interest, to gas chromatography prior to mass spectrometric analysis.

Liquid chromatography (LC) including high-performance liquid chromatography (HPLC) rely on relatively slow, laminar flow technology. Traditional HPLC analysis relies on column packings in which laminar flow of the sample through the column is the basis for separation of the analyte of interest from the sample. The skilled artisan will understand that separation in such columns is a diffusional process. HPLC has been successfully applied to the separation of compounds in biological samples. But a significant amount of sample preparation is required prior to the separation and subsequent analysis with a mass spectrometer (MS), making this technique labor intensive. In addition, most HPLC systems do not utilize the mass spectrometer to its fullest potential, allowing only one HPLC system to be connected to a single MS instrument, resulting in lengthy time requirements for performing a large number of assays.

Various methods have been described involving the use of HPLC for sample clean-up prior to mass spectrometry analysis. See, e.g., Taylor et al., *Therapeutic Drug Monitoring* 22:608-12 (2000) (manual precipitation of blood samples, followed by manual C18 solid phase extraction, injection into an HPLC for chromatography on a C18 analytical column, and MS/MS analysis); and Salm et al, *Clin. Therapeutics* 22 Supl. B:B71-B85 (2000) (manual precipitation of blood samples, followed by manual C18 solid phase extraction, injection into an HPLC for chromatography on a C18 analytical column, and MS/MS analysis).

One of skill in the art can select HPLC instruments and columns that are suitable for use in the invention. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties. One suitable bonded surface is a hydrophobic bonded surface such as an alkyl bonded surface. Alkyl bonded surfaces may include C-4, C-8, or C-18 bonded alkyl groups, preferably C-18 bonded groups. The chromatographic column includes an inlet port for receiving a sample and an outlet port for discharging an effluent that includes the fractionated sample. In one embodiment, the sample (or pre-purified sample) is applied to the column at the inlet port, eluted with a solvent or solvent mixture, and discharged at the outlet port. Different solvent modes may be selected for eluting the analytes of interest. For example, liquid chromatography may be performed using a gradient mode, an isocratic mode, or a polytyptic (i.e. mixed) mode. During chromatography, the separation of materials is effected by variables such as choice of eluent (also known as a "mobile phase"), choice of gradient elution and the gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

Recently, high turbulence liquid chromatography ("HTLC"), also called high throughput liquid chromatography, has been applied for sample preparation prior to analysis by mass spectrometry. See, e.g., Zimmer et al., *J. Chromatogr. A* 854:23-35 (1999); see also, U.S. Pat. Nos. 5,968,367; 5,919,368; 5,795,469; and 5,772,874. Traditional HPLC analysis relies on column packings in which laminar flow of the sample through the column is the basis for separation of the analyte of interest from the sample. The skilled artisan will understand that separation in such columns is a diffusional process. In contrast, it is believed that turbulent flow, such as that provided by HTLC columns and methods, may enhance the rate of mass transfer, improving the separation characteristics provided. In some embodiments, high turbulence liquid chromatography (HTLC), alone or in combination with one or more purification methods, may be used to purify the dihydroxyvitamin D metabolite of interest prior to mass spectrometry. In such embodiments samples may be extracted using an HTLC extraction cartridge which captures the analyte, then eluted and chromatographed on a second HTLC column or onto an analytical HPLC column prior to ionization. Because the steps involved in these chromatography procedures can be linked in an automated fashion, the requirement for operator involvement during the purification of the analyte can be minimized. In certain embodiments of the method, samples are subjected to protein precipitation as described above prior to loading on the HTLC column; in alternative embodiments, the samples may be loaded directly onto the HTLC without being subjected to protein precipitation.

Recently, research has shown that epimerization of the hydroxyl group of the A-ring of vitamin $D_3$ metabolites is an important aspect of vitamin $D_3$ metabolism and bioactivation, and that depending on the cell types involved, 3-C epimers of vitamin $D_3$ metabolites (e.g., 3-epi-25(OH)$D_3$; 3-epi-24,25 (OH)$_2D_3$; and 3-epi-1,25(OH)$_2D_3$) are often major metabolic products. See Kamao et al., *J. Biol. Chem.*, 279:15897-15907 (2004). Kamao et al., further provides methods of separating various vitamin D metabolites, including 3-C epimers, using Chiral HPLC. Accordingly, the invention also provides methods of detecting the presence, absence and/or amount of a specific epimer of one or more vitamin D metabolites, preferably vitamin $D_3$ metabolites, in a sample by (1) separating one or more specific vitamin D metabolites by chiral chromatography, preferably chiral HPLC; and (2) detecting the presence and/or amount of one or more vitamin D metabolites using mass spectrometry methods as described herein. The chiral chromatography procedures described in Kamao et al., are suitable for the methods of the invention, however, one of ordinary skill in the art understands that there are numerous other chiral chromatography methods that would also be suitable. In preferred embodiments the method includes, separating 25(OH)D$_3$ from 3-epi-25(OH)D$_3$, if present in a sample, using chiral chromatography; and detecting the presence and/or amount of the 25(OH)D$_3$ and the 3-epi-25(OH)D$_3$ in the sample using mass spectrometry. In related embodiments, the method includes separating 1α,25(OH)$_2$D$_3$ from 3-epi-1α,25(OH)$_2$D$_3$, if present in a sample, using chiral chromatography; and detecting the presence and/or amount of the 1α,25(OH)$_2$D$_3$ and the 3-epi-1α,25(OH)$_2$D$_3$ in the sample using mass spectrometry. In certain embodiments of the invention, chiral chromatography is used in conjunction with the HTLC methods described above.

Detection and Quantitation by Mass Spectrometry

Disclosed are methods for detecting the presence or amount of one or more dihydroxyvitamin D metabolites in a sample. In certain aspects the method involves ionizing the dihydroxyvitamin D metabolite(s), detecting the ion(s) by mass spectrometry, and relating the presence or amount of the ion(s) to the presence or amount of the dihydroxyvitamin D metabolite(s) in the sample. The method may include (a) purifying a dihydroxyvitamin D metabolite, if present in the sample, (b) ionizing the purified dihydroxyvitamin D metabolite and (c) detecting the presence or amount of the ion, wherein the presence or amount of the ion is related to the presence or amount of the dihydroxyvitamin D metabolite in the sample. In preferred embodiments, the ionizing step (b) may include (i) ionizing a dihydroxyvitamin D metabolite, if present in the sample, to produce an ion; (ii) isolating the dihydroxyvitamin D metabolite ion by mass spectrometry to provide a precursor ion; and (iii) effecting a collision between the isolated precursor ion and an inert collision gas to produce at least one fragment ion detectable in a mass spectrometer. In certain preferred embodiments the precursor ion is a protonated and dehydrated ion of the dihydroxyvitamin D metabolite.

Further provided is a method for determining the presence or amount of a dihydroxyvitamin D metabolite in a test sample by tandem mass spectrometry. The method may involve (a) generating a protonated and dehydrated precursor ion of the dihydroxyvitamin D metabolite; (b) generating one or more fragment ions of the precursor ion; and (c) detecting the presence or amount of one or more of the ions generated in step (a) or (b) or both and relating the detected ions to the presence or amount of the dihydroxyvitamin D metabolite in the sample.

In certain preferred embodiments of the invention, at least one fragment ion is detected, wherein the presence or amount of the precursor and/or at least one fragment ion is related to the presence or amount of the dihydroxyvitamin D metabolite in the sample. Preferably at least one fragment ion is specific for the dihydroxyvitamin D metabolite of interest. In some embodiments, the methods of the invention can be used to detect and quantify two or more dihydroxyvitamin D metabolites in a single assay.

Mass spectrometry is performed using a mass spectrometer which includes an ion source for ionizing the fractionated sample and creating charged molecules for further analysis. For example ionization of the sample may be performed by electrospray ionization (ESI), atmospheric pressure chemical ionization (APCI), photoionization, electron ionization, fast atom bombardment (FAB)/liquid secondary ionization (LSIMS), matrix assisted laser desorption ionization (MALDI), field ionization, field desorption, thermospray/plasmaspray ionization, and particle beam ionization. The skilled artisan will understand that the choice of ionization method can be determined based on the analyte to be measured, type of sample, the type of detector, the choice of positive versus negative mode, etc.

After the sample has been ionized, the positively charged or negatively charged ions thereby created may be analyzed to determine a mass-to-charge ratio (i.e., m/z). Suitable analyzers for determining mass-to-charge ratios include quadropole analyzers, ion traps analyzers, and time-of-flight analyzers. The ions may be detected using several detection modes. For example, selected ions may be detected (i.e., using a selective ion monitoring mode (SIM)), or alternatively, ions may be detected using a scanning mode, e.g., multiple reaction monitoring (MRM) or selected reaction monitoring (SRM). Preferably, the mass-to-charge ratio is determined using a quadropole analyzer. For example, in a "quadrupole" or "quadrupole ion trap" instrument, ions in an oscillating radio frequency field experience a force proportional to the DC potential applied between electrodes, the amplitude of the RF signal, and m/z. The voltage and amplitude can be selected so that only ions having a particular m/z travel the length of the quadrupole, while all other ions are deflected. Thus, quadrupole instruments can act as both a "mass filter" and as a "mass detector" for the ions injected into the instrument.

One may enhance the resolution of the MS technique by employing "tandem mass spectrometry," or "MS/MS." In this technique, a precursor ion (also called a parent ion) generated from a molecule of interest can be filtered in an MS instrument, and the precursor on is subsequently fragmented to yield one or more fragment ions (also called daughter ions or product ions) that are then analyzed in a second MS procedure. By careful selection of precursor ions, only ions produced by certain analytes are passed to the fragmentation chamber, where collision with atoms of an inert gas to produce the daughter ions. Because both the precursor and fragment ions are produced in a reproducible fashion under a given set of ionization/fragmentation conditions, the MS/MS technique can provide an extremely powerful analytical tool. For example, the combination of filtration/fragmentation can be used to eliminate interfering substances, and can be particularly useful in complex samples, such as biological samples.

Additionally, recent advances in technology, such as matrix-assisted laser desorption ionization coupled with time-of-flight analyzers ("MALDI-TOF") permit the analysis of analytes at femtomole levels in very short ion pulses. Mass spectrometers that combine time-of-flight analyzers with tandem MS are also well known to the artisan. Additionally, multiple mass spectrometry steps can be combined in methods known as "MS/MS"." Various other combinations may be employed, such as MS/MS/TOF, MALDI/MS/MS/TOF, or SELDI/MS/MS/TOF mass spectrometry.

The mass spectrometer typically provides the user with an ion scan; that is, the relative abundance of each ion with a particular m/z over a given range (e.g., 100 to 1000 amu). The results of an analyte assay, that is, a mass spectrum, can be related to the amount of the analyte in the original sample by numerous methods known in the art. For example, given that sampling and analysis parameters are carefully controlled, the relative abundance of a given ion can be compared to a table that converts that relative abundance to an absolute amount of the original molecule. Alternatively, molecular standards can be run with the samples, and a standard curve constructed based on ions generated from those standards. Using such a standard curve, the relative abundance of a given ion can be converted into an absolute amount of the original molecule. In certain preferred embodiments, an internal standard is used to generate a standard curve for calculating the quantity of the dihydroxyvitamin D metabolite. Methods of generating and using such standard curves are well known in the art and one of ordinary skill is capable of selecting an appropriate internal standard. For example, an isotope of a dihydroxyvitamin D metabolite may be used as an internal standard, in preferred embodiments the dihydroxyvitamin D metabolite is a deuterated dihydroxyvitamin D metabolite, for example $1\alpha,25(OH)_2D_2\text{-}[26,26,26,27,27,27]\text{-}^2H$ or $1\alpha,25(OH)_2D_3\text{-}[6,19,19']\text{-}^2H$ or both. Numerous other methods for relating the presence or amount of an ion to the presence or amount of the original molecule will be well known to those of ordinary skill in the art.

One or more steps of the methods of the invention can be performed using automated machines. In certain embodiments, one or more purification steps are performed on line, and more preferably all of the purification and mass spectrometry steps may be performed in an on-line fashion.

In certain embodiments, such as MS/MS, where precursor ions are isolated for further fragmentation, collision activation dissociation is often used to generate the fragment ions for further detection. In CAD, precursor ions gain energy through collisions with an inert gas, and subsequently fragment by a process referred to as "unimolecular decomposition". Sufficient energy must be deposited in the precursor ion so that certain bonds within the ion can be broken due to increased vibrational energy.

In particularly preferred embodiments dihydroxyvitamin D metabolites are detected and/or quantified using LC-MS/MS as follows. The samples are subjected to liquid chromatography, preferably HPLC, the flow of liquid solvent from the chromatographic column enters the heated nebulizer interface of a LC-MS/MS analyzer and the solvent/analyte mixture is converted to vapor in the heated tubing of the interface. The analytes (i.e. dihydroxyvitamin D metabolites), contained in the nebulized solvent, are ionized by the corona discharge needle of the interface, which applies a large voltage to the nebulized solvent/analyte mixture. The ions, i.e. precursor ions, pass through the orifice of the instrument and enter the first quadrupole. Quadrupoles 1 and 3 (Q1 and Q3) are mass filters, allowing selection of ions (i.e., "precursor" and "fragment" ions) based on their mass to charge ratio (m/z). Quadrupole 2 (Q2) is the collision cell, where ions are fragmented. The first quadrupole of the mass spectrometer (Q1) selects for molecules with the mass to charge ratios of the specific dihydroxyvitamin D metabolites to be analyzed. Precursor ions with the correct m/z ratios of the precursor ions of specific dihydroxyvitamin D metabolites are allowed to pass into the collision chamber (Q2), while unwanted ions with any other m/z collide with the sides of the quadrupole and are eliminated. Precursor ions entering Q2 collide with neutral Argon gas molecules and fragment. This process is called Collision Activated Dissociation (CAD). The fragment ions generated are passed into quadrupole 3 (Q3), where the fragment ions of the desired dihydroxyvitamin D metabolites are selected while other ions are eliminated.

The methods of the invention may involve MS/MS performed in either positive or negative ion mode. Using standard methods well known in the art, one of ordinary skill is capable of identifying one or more fragment ions of a particular precursor ion of a dihydroxyvitamin D metabolite that can be used for selection in quadrupole 3 (Q3).

If the precursor ion of a dihydroxyvitamin D metabolite of interest includes an alcohol or amine group, fragment ions are commonly formed that represent a dehydration or deamination of the precursor ion, respectfully. In the case of precursor ions that include an alcohol group, such fragment ions formed by dehydration are caused by a loss of one or more water molecules from the precursor ion (i.e., where the difference in m/z between the precursor ion and fragment ion is about 18 for the loss of one water molecule, or about 36 for the loss of two water molecules, etc.). In the case of precursor ions that include an amine group, such fragment ions formed by deamination are caused by a loss of one or more ammonia molecules (i.e. where the difference in m/z between the precursor ion and fragment ion is about 17 for the loss of one ammonia molecule, or about 34 for the loss of two ammonia molecules, etc.). Likewise, precursor ions that include one or more alcohol and amine groups commonly form fragment ions that represent the loss of one or more water molecules and/or one or more ammonia molecules (e.g., where the difference in m/z between the precursor ion and fragment ion is about 35 for the loss of one water molecule and the loss of one ammonia molecule). Generally, the fragment ions that represent dehydrations or deaminations of the precursor ion are not specific fragment ions for a particular analyte.

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC methods. The areas under the peaks corresponding to particular ions, or the amplitude of such peaks, are measured and the area or amplitude is correlated to the amount of the analyte (vitamin D metabolite) of interest. In certain embodiments, the area under the curves, or amplitude of the peaks, for fragment ion(s) and/or precursor ions are measured to determine the amount of a dihydroxyvitamin D metabolite. As described above, the relative abundance of a given ion can be converted into an absolute amount of the original analyte, i.e., dihydroxyvitamin D metabolite, using calibration standard curves based on peaks of one or more ions of an internal molecular standard, such as $^6D\text{-}25OHD_3$.

In certain aspects of the invention, the quantity of various ions is determined by measuring the area under the curve or the amplitude of the peak and a ratio of the quantities of the ions is calculated and monitored (i.e. "daughter ion ratio monitoring"). In certain embodiments of the method, the ratio(s) of the quantity of a precursor ion and the quantity of one or more fragment ions of a dihydroxyvitamin D metabolite can be calculated and compared to the ratio(s) of a molecular standard of the dihydroxyvitamin D metabolite similarly measured. In embodiments where more than one fragment ion of a dihydroxyvitamin D metabolite is monitored, the ratio(s) for different fragment ions may be determined instead of, or in addition to, the ratio of the fragment ion(s) compared to the precursor ion. In embodiments where such ratios are monitored, if there is a substantial difference in an ion ratio in the sample as compared to the molecular standard, it is likely that a molecule in the sample is interfering with the results. To the contrary, if the ion ratios in the sample and the molecular standard are similar, then there is increased confidence that there is no interference. Accordingly, monitoring such ratios in the samples and comparing the ratios to those of authentic molecular standards may be used to increase the accuracy of the method.

In particularly preferred embodiments of the invention, the presence or absence or amount of two or more dihydroxyvitamin D metabolites in a sample are detected in a single assay using the above described MS/MS methods.

The following examples serve to illustrate the invention. These examples are in no way intended to limit the scope of the invention.

EXAMPLES

Example 1

Determination of 1α,25-dihydroxyvitamin $D_3$ and 1α,25-dihydroxyvitamin $D_2$ by LC-MS/MS 50 μl of an internal standard mixture (stripped serum spiked with 1α,25(OH)2D3-[6,19,19]-2H at 50 pg/50 microliters and 1α,25(OH)2D2-[26,26,26,27,27,27]-2H at 200 pg/50 microliters) was added to test tubes then 500 μl of calibrator solution, quality control test solution, or serum standard, followed by the internal standard mixture. The solutions were delipidized by adding 50 μl $MgCl_2$/dextran sulfate solution and mixing thoroughly. The tubes were then centrifuged for 20 minutes and 500 μl of supernatant was transferred to ImmunoTube cartridges containing anti-dihydroxyvitamin D immunocapsules from ALPCO Diagnostics (Catalog Number K2113.SI). The cartridges were incubated on a shaker at room temperature for two hours. The beads were then washed three times with 750 μl deionized water. The beads were drained between washes by centrifuging the cartridges. Dihydroxyvitamin D bound to the beads was eluted with 250 μl ethanol directly into a glass HPLC insert and then dried to completion under nitrogen. The samples were then derivatized by adding 50 μl of 50 microliters of 4-phenyl-1,2,4-triazoline-3,5-dione (PTAD) solution (0.8 mg/mL in acetonitrile). The derivitization reaction was stopped by adding 50 μl deionized water.

The HPLC inserts were then transferred to an HPLC autosampler for loading to the LC-MS/MS analyzer. LC-MS/MS was performed using a Thermo Finnigan LC-MS/MS analyzer (Thermo Finnigan Quantum TSQ (S/N: TQU00655)) with an atmospheric pressure chemical ionization (APCI) source as the detector. An autosampler was used to inject 90 μL of extracted sample supernatant onto an HPLC column. Liquid chromatography was performed with a Synergi™ Max-RP C-12 Phenomenex columns run at 0.8 mL/minute. Two mobile phase solutions were used for the HPLC: mobile phase A was 0.1% formic acid in HPLC-grade water and mobile phase B was 100% acetonitrile. The total run time was 5.00 min with the collection window between 1:31-2:31 (60 seconds). The starting condition (20 seconds) was 50% mobile phase A and 50% mobile phase B; the gradient (160 seconds) was from 50% mobile phase A and 50% mobile phase B to 2% mobile phase A and 98% mobile phase B; the wash step (60 seconds) was 2% mobile phase A and 98% mobile phase B; and the reconditioning step was 50% mobile phase A and 50% mobile phase B.

The flow of liquid solvent exiting the HPLC column entered the heated nebulizer interface of the Thermo Finnigan LC-MS/MS analyzer and the dihydroxyvitamin D metabolites were measured using APCI in positive mode. The solvent/analyte mixture was first converted to vapor in the heated tubing of the interface. The analytes, contained in the nebulized solvent, were ionized (a positive charge added) by the corona discharge needle of the interface, which applies a large voltage to the nebulized solvent/analyte mixture. The ions pass through the orifice of the instrument and enter the first quadrupole. Quadrupoles 1 and 3 (Q1 and Q3) are mass filters, allowing selection of ions based on their mass to charge ratio (m/z). Quadrupole 2 (Q2) is the collision cell, where the ions are fragmented.

The first quadrupole of the mass spectrometer (Q1) selected for molecules with the mass to charge ratios of 1α,25 $(OH)_2D_2$, 1α,25$(OH)_2D_3$, $^6$D-1α,25$(OH)_2D_2$ (internal standard) and -1α,25$(OH)_2D_3$ (internal standard). Ions with these m/z ratios (see table below) were allowed to pass into the collision chamber (Q2), while unwanted ions with any other m/z collide with the sides of the quadrupole and are eliminated. Ions entering Q2 collide with neutral Argon gas molecules and fragment. The fragment ions generated are passed into quadrupole 3 (Q3), where the fragment ions of 1α,25 $(OH)_2D_2$, 1α,25$(OH)_2D_3$, $^6$D-1α,25$(OH)_2D_2$ (internal standard) and -1α,25$(OH)_2D_3$ (internal standard) were selected (see table below) and other ions are eliminated. The following mass transitions were used for detection and quantitation during validation:

TABLE 1

Mass transitions for selected dihydroxyvitamin D metabolites

| Analyte | Precursor Ion | Product Ion |
|---|---|---|
| 1α,25$(OH)_2D_3$ | 574.37 | 314.12 |
| 1α,25$(OH)_2D_3$-[6,19,19']-$^2$H (Internal Standard) | 577.37 | 317.12 |
| 1α,25$(OH)_2D_2$ | 586.37 | 314.12 |
| 1α,25$(OH)_2D_2$-[26,26,26,27,27,27]-$^2$H (Internal Standard) | 592.37 | 314.12 |

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC methods.

Area ratios of the analyte and internal standards (1α,25 (OH)2D3-[6,19,19']-2H and 1α,25$(OH)_2D_2$-[26,26,26,27,27,27]-$^2$H) peaks were used to construct calibration curves, which were then used to calculate analyte concentrations. Using the calibration curves, the concentrations of 1α,25 $(OH)_2D_2$ and 1α,25$(OH)_2D_3$ were quantitated in the patient samples.

Example 2

Intra-Assay and Inter-Assay Precision

Stock solutions of 1α,25$(OH)_2D_2$ and 1α,25$(OH)_2D_3$ were added to pooled serum to produce a Low Pool (10-15 ng/mL of each metabolite), a Medium-Low Pool (25-35 ng/mL of each metabolite), Medium-High Pool (55-65 ng/mL of each metabolite) and a High Pool (115-130 ng/mL). Four aliquots from each of the Low, Medium-Low, Medium-High and High Pools were analyzed in a single assay using the LC-MS/MS protocols described in Example 1. The following precision values were determined:

TABLE 2

Intra-Assay Variation: 1α,25-Dihydroxyvitamin $D_2$ (1α,25$(OH)_2D_2$)

|  | Low | Medium-Low | Medium-High | High |
|---|---|---|---|---|
| 1 | 12 | 30 | 68 | 141 |
| 2 | 15 | 26 | 61 | 125 |
| 3 | 11 | 35 | 63 | 110 |
| 4 | 11 | 32 | 67 | 96 |
| Average (ng/mL) | 12.4 | 30.6 | 63.7 | 118.1 |
| CV (%) | 16.2% | 11.8% | 5.3% | 16.5% |

TABLE 3

Intra-Assay Variation: 1α,25-Dihydroxyvitamin $D_3$ (1α,25$(OH)_2D_3$)

|  | Low | Medium-Low | Medium-High | High |
|---|---|---|---|---|
| 1 | 10 | 30 | 68 | 125 |
| 2 | 14 | 33 | 59 | 138 |
| 3 | 11 | 35 | 56 | 116 |
| 4 | 15 | 30 | 59 | 118 |
| Average (ng/mL) | 12.3 | 32.1 | 60.6 | 124.2 |
| CV (%) | 17.8% | 8.1% | 8.6% | 8.2% |

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

That which is claimed is:

1. A method for determining the amount of 1α,25 dihydroxyvitamin $D_2$ (1α,25$(OH)_2D_2$) in a biological sample, when taken from a human, by tandem mass spectrometry, comprising:
    (a) processing a biological sample from a human by one or more methods to generate a processed sample, wherein at least one method used is derivatizing 1α,25$(OH)_2D_2$ with 4-phenyl-1,2,4-triazoline-3,5-dione (PTAD);
    (b) enriching derivatized 1α,25$(OH)_2D_2$ from step (a) by high performance liquid chromatography (HPLC);
    (c) generating a precursor ion of the derivatized 1α,25$(OH)_2 D_2$ obtained from step (b) wherein said precursor ion has a mass/charge ratio of 586.37±0.5;
    (d) generating one or more fragment ions of said precursor ion, wherein at least one of said one or more fragment ions comprise an ion having a mass/charge ratio of 314.12±0.5; and
    (e) detecting the amount of one or more of said ions generated in step (c) or (d) or both by mass spectrometry and relating the detected ions to the amount of said 1α,25$(OH)_2D_2$ in said biological sample from a human.

2. The method of claim 1, wherein said processing further comprises enriching 1α,25$(OH)_2D_2$ by immunopurification prior to derivatization.

3. The method of claim 1, wherein the method further comprises determining the amount of 1α,25 dihydroxyvitamin $D_3$ (1α,25$(OH)_2D_3$) in said biological sample from a human by tandem mass spectrometry.

4. The method of claim 3, wherein said 1α,25$(OH)_2D_3$ is derivatized with 4-phenyl-1,2,4-triazoline-3,5-dione (PTAD) prior to mass spectrometry; and wherein said precursor ion of said 1α,25$(OH)_2D_3$ has a mass/charge ratio of 574.37±0.5.

5. The method of claim 1, wherein said biological sample comprises plasma or serum.

6. The method of claim 1, wherein said generating a precursor ion comprises ionizing by atmospheric pressure chemical ionization (APCI).

7. A method for determining the amount of 1α,25 dihydroxyvitamin $D_3$ (1α,25$(OH)_2D_3$) in a biological sample, when taken from a human, by tandem mass spectrometry, comprising:
    (a) processing a biological sample from a human by one or more methods to generate a processed sample, wherein at least one method used is derivatizing 1α,25$(OH)_2D_3$ with 4-phenyl-1,2,4-triazoline-3,5-dione (PTAD);
    (b) purifying the derivatized 1α,25$(OH)_2D_3$ from step (a) by high performance liquid chromatography (HPLC);
    (c) generating a precursor ion of the derivatized 1α,25$(OH)_2 D_3$ having a mass/charge ratio of 574.37±0.5;
    (d) generating one or more fragment ions of said precursor ion, wherein at least one of said one or more fragment ions comprise an ion having a mass/charge ratio of 314.12±0.5; and
    (e) detecting the amount of one or more of said ions generated in step (c) or (d) or both by mass spectrometry and relating the detected ions to the amount of said 1α,25$(OH)_2D_3$ in said biological sample from a human.

8. The method of claim 7, wherein said processing further comprises enriching 1α,25$(OH)_2D_2$ by immunopurification prior to derivatization.

9. The method of claim 7, wherein the method further comprises determining the amount of 1α,25 dihydroxyvitamin $D_2$ (1α,25$(OH)_2D_2$) in said biological sample from a human.

10. The method of claim 9, wherein 1α,25$(OH)_2D_2$ is derivatized with PTAD prior to mass spectrometry; and wherein said precursor ion of said 1α,25$(OH)_2D_2$ has a mass/charge ratio of 586.37±0.5.

11. The method of claim 7, wherein said generating a precursor ion comprises ionizing by atmospheric pressure chemical ionization (APCI).

12. A method for determining the amount of 1α,25 dihydroxyvitamin $D_2$ (1α,25$(OH)_2D_2$) in a biological sample, when taken from a human, by tandem mass spectrometry, comprising:
    (a) processing a biological sample from a human by one or more methods to generate a processed sample, wherein at least one method used is enriching 1α,25$(OH)_2D_2$ by high performance liquid chromatography (HPLC);

(b) generating a precursor ion of the $1\alpha,25(OH)_2D_2$ obtained from step (a) having a mass/charge ratio of 411.35±0.5;

(c) generating one or more fragment ions of said precursor ion, wherein said one or more fragment ions comprise one or more ions selected from the group consisting of ions having a mass/charge ratio of 151.12±0.5 and 135.12±0.5; and (d) detecting the amount of one or more of said ions generated in step (b) or (c) or both by mass spectrometry and relating the detected ions to the amount of said $1\alpha,25(OH)_2D_2$ in said biological sample from a human;

wherein $1\alpha,25(OH)_2D_2$ is not derivatized prior to mass spectrometry.

13. The method of claim 12, wherein said processing of step (a) further comprises enriching $1\alpha,25(OH)_2D_2$ by immunopurification.

14. The method of claim 12, wherein the method further comprises determining the amount of $1\alpha,25$ dihydroxyvitamin $D_3$ ($1\alpha,25(OH)_2D_3$) in said biological sample from a human.

15. The method of claim 14, wherein said $1\alpha,25(OH)_2D_3$ is not derivatized prior to mass spectrometry; and wherein said precursor ion of said $1\alpha,25(OH)_2D_3$ has a mass/charge ratio of 399.35±0.5.

16. The method of claim 12, wherein said biological sample comprises plasma or serum.

17. The method of claim 12, wherein said generating a precursor ion comprises ionizing by atmospheric pressure chemical ionization (APCI).

18. A method for determining the amount of $1\alpha,25$ dihydroxyvitamin $D_3$ ($1\alpha,25(OH)_2D_3$) in a biological sample, when taken from a human, by tandem mass spectrometry, comprising:

(a) processing a biological sample from a human by one or more methods to generate a processed sample, wherein at least one method used is enriching $1\alpha,25(OH)_2D_3$ by high performance liquid chromatography (HPLC);

(b) generating a precursor ion of the $1\alpha,25(OH)_2D_3$ obtained from step (a) having a mass/charge ratio of 399.35±0.5;

(c) generating one or more fragment ions of said precursor ion, wherein said one or more fragment ions comprise one or more ions selected from the group consisting of ions having a mass/charge ratio of 151.12±0.5 and 135.12±0.5; and (d) detecting the amount of one or more of said ions generated in step (b) or (c) or both by mass spectrometry and relating the detected ions to the amount of said $1\alpha,25(OH)_2D_3$ in said biological sample from a human;

wherein $1\alpha,25(OH)_2D_3$ is not derivatized prior to mass spectrometry.

19. The method of claim 18, wherein said processing of step (a) further comprises enriching $1\alpha,25(OH)_2D_3$ by immunopurification.

20. The method of claim 18, wherein the method further comprises determining the amount of $1\alpha,25$ dihydroxyvitamin $D_2$ ($1\alpha,25(OH)_2D_2$) in said biological sample from a human.

21. The method of claim 20, wherein said $1\alpha,25(OH)_2D_2$ is not derivatized prior to mass spectrometry; and wherein said precursor ion of said $1\alpha,25(OH)_2D_2$ has a mass/charge ratio of 411.35±0.5.

22. The method of claim 18, wherein said biological sample comprises plasma or serum.

23. The method of claim 18, wherein said generating a precursor ion comprises ionizing by atmospheric pressure chemical ionization (APCI).

24. The method of claim 1, wherein said processing further comprises enriching derivatized $1\alpha,25(OH)_2D_2$ by high turbulence liquid chromatography (HTLC).

25. The method of claim 7, wherein said biological sample comprises plasma or serum.

26. The method of claim 7, wherein said processing further comprises enriching derivatized $1\alpha,25(OH)_2D_3$ by high turbulence liquid chromatography (HTLC).

* * * * *